United States Patent
Gobbi et al.

(10) Patent No.: US 6,175,642 B1
(45) Date of Patent: *Jan. 16, 2001

(54) DEVICE FOR AUTOMATICALLY POSITIONING AND CENTERING A MICROSCOPE OPTICAL HEAD

(75) Inventors: Pier Giorgio Gobbi, Pavia; Marco Carena, Milan; Alberto Fortini, Milan; Claudio Azzolini, Milan; Rosario Brancato, Milan, all of (IT)

(73) Assignee: Fondazione Centro S. Raffaele Del Monte Tabor, Milan (IT)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/639,751

(22) Filed: Apr. 29, 1996

(30) Foreign Application Priority Data

Apr. 28, 1995 (IT) .............................................. MI95A0864

(51) Int. Cl.⁷ ....................................................... G06K 9/00
(52) U.S. Cl. ............................ 382/128; 348/172; 359/656
(58) Field of Search ...................... 382/128, 133, 382/134, 103, 107; 359/363, 368, 369, 371, 385, 386, 391, 362, 372, 374, 375, 376, 377, 397, 656, 696–698; 606/4, 1, 2; 128/897, 898; 348/61, 77–79, 169–172; 351/206, 208, 210, 221; 396/14, 18

(56) References Cited

U.S. PATENT DOCUMENTS

| | | | |
|---|---|---|---|
| 4,375,674 | * 3/1983 | Thorton .................................. | 702/41 |
| 4,499,597 | * 2/1985 | Alves .................................... | 382/205 |
| 4,849,906 | * 7/1989 | Chodos et al. ....................... | 348/171 |
| 4,958,939 | * 9/1990 | Samad .................................. | 382/223 |
| 5,055,926 | * 10/1991 | Christensen et al. ................ | 358/125 |
| 5,144,688 | * 9/1992 | Bovir et al. .......................... | 382/232 |
| 5,196,688 | * 3/1993 | Hesse et al. ....................... | 250/203.6 |
| 5,216,500 | | 6/1993 | Krummey et al. ...................... 358/93 |
| 5,293,574 | * 3/1994 | Roehm et al. ...................... | 378/98.2 |
| 5,655,029 | * 8/1997 | Rutenberg et al. .................. | 382/133 |
| 5,661,598 | * 8/1997 | Tomioka .............................. | 359/388 |

FOREIGN PATENT DOCUMENTS

| | | | |
|---|---|---|---|
| 36 20 887 | 12/1987 | (DE) | .............................. G01N/35/02 |
| 0 229 581 | * 7/1987 | (EP) . | |

OTHER PUBLICATIONS

Chacha, P.B., Operating Microscope, Microsurgical Instruments and Microsutures, Annals Of the Academy of Medicine, abstract, Oct. 1979.*

Reinhardt et al., Stereo–Microvision. Development of an Opto–Electronic Operating Microscope, Bildgebung, pp. 105–109, Jun. 1993.*

Zamorano et al., Interactive Intraoperative Localization Using an Infrared–Based System, Stereotactic and Functional Neurosurgery, abstract, 1994.*

* cited by examiner

*Primary Examiner*—Jon Chang
*Assistant Examiner*—Jayanti K. Patel
(74) *Attorney, Agent, or Firm*—Oblon, Spivak, McClelland, Maier & Neustadt, P.C.

(57) ABSTRACT

A device for automatically positioning and centering the optical head of a microscope, for example for surgical use, the optical head being connected to a drive unit. This device analyzes the image framed by the microscope objective by use of an automatic system for analyzing the image light distribution, for example a video camera connected to a processing circuit and possibly to a microprocessor, then processes the image until a reference point of the light distribution is identified by dividing the image into N subzones. Then, on the basis of information regarding the position of the reference point, the device controls the drive unit of the microscope optical head to return the reference point to within a predetermined tolerance zone, if possible.

31 Claims, 1 Drawing Sheet

DEVICE FOR AUTOMATICALLY POSITIONING AND CENTERING A MICROSCOPE OPTICAL HEAD

BACKGROUND OF THE INVENTION

This invention relates to a device for automatically positioning the optical head of a surgical microscope relative to the operating site.

Microsurgical techniques and methods are widespread in many specialist sectors of medical science, such as neurosurgery, ophthalmology, reconstructive hand and foot surgery, etc. The common denominator is the use of an optical microscope in the operating theater for suitably magnifying the anatomical details of the part subjected to surgery.

An operating microscope consists essentially of an objective and a pair of "tube lenses". When the object to be observed is placed in the focal plane of the objective, these lenses reproduce an intermediate image of it which can be observed and/or magnified by a pair of oculars. Tube lenses and oculars are provided as a pair to allow the object to be viewed stereoscopically.

Normally between the objective and tube lenses there is inserted a revolving turret with Galilean telescopes or a pancratic system to be able to vary, respectively discretely or continuously, the resultant total magnification of the microscope. Typical magnifications are between 5 and 50. Frequently the magnification system is operated by a motorized system, suitably controlled by a keypad.

The optical head of the microscope is completed by a coaxial illumination system for the operating field. The optical head is mechanically suspended from an articulated arm rigid with a stand rigidly connected to the ceiling or to a suitable base rigid with the floor. To be able to be freely positioned over the operating couch, the microscope is provided with a system for fine translation in the vertical direction (for focusing) and in the two horizontal directions (for image centering). Frequently such movements are effected by electric motors controlled by a pedal board available to the surgeon.

The microscope optical head can be provided with an image divider, making a further two observation channels available. It is normal practice to install an additional pair of oculars for use by a second operator and a photographic or television apparatus for acquiring visual documentation of the microsurgery.

Using a modular system it is possible in reality to install on the same microscope a number of image dividers, and to connect to each of them either an additional pair of oculars or a photographic, television or other apparatus which can be considered useful. It should be noted that the field of vision on the recording channel is usually smaller than that available to the primary operator, because of the different configuration of the optical systems forming the image. This means that the microscope objective must be centered as accurately as possible on the zone of interest to the operation. In this respect, where the surgeon is still able to "see", it is not automatically certain that the eye of the telecamera or photographic apparatus is able to receive a sharp and reproducible image.

If the area of surgical interest leaves the field of vision of the operator, or of the recording system (for example reproduced on a monitor by a telecamera), the surgeon himself or herself, or rather one of his or her assistants, operates the translation motors to return the image of interest to the center of the field of vision. This is not always easy, and in particular could take too much time. It can hence happen that the surgeon loses vision of the field of operating interest for a few moments, with consequent obvious inconvenience, or the loss of important operating stages in the archive of photographic images or visual recording.

The fact of the area of surgical interest leaving the field of vision of the operator can have various causes. In general it can happen either because the site of the surgical treatment has effectively changed or because, although this site has remained unchanged, that part of the body on which the operation is being carried out has shifted for strictly anatomical reasons.

A typical surgical operation in which this often happens is vitreo-retinal endoscopic surgery, in which the field of operation is the rear chamber of the eyeball.

During vitreo-retinal endoscopic operations, the surgeon introduces into the eyeball not only the operating instruments but also, according to requirements, draining or infusion probes, or lighting systems such as a fiber optic endoscopic probe.

In this type of operation, the entire part on which surgery is to be carried out cannot always fall within the visual and recording field of the microscope. This is even more so the case when operating with high magnification. It often happens that the position of the microscope optical head has to be readjusted as a result of the shifting of the operation site. Again, because of the anatomy of the organ subjected to surgery (i.e. the eyeball) and of the considerable freedom of rotation of the eyeball within its socket, it can happen that although the surgery remains on the same portion of tissue, the eyeball undergoes considerable rotation within its socket, for example because of surgical maneuvers by the surgeon. This can shift the image of interest outside the field of vision.

Given the relative frequency of such movements, reiterated adjustments of the microscope position are required, to the detriment of the attention and comfort of the surgeon, in addition to the detriment of the quality of the images being acquired.

SUMMARY OF THE INVENTION

An object of the present invention is to obviate the aforesaid problems of the state of the art.

A particular object of the present invention is to provide a device to be connected to a surgical microscope which acts on the microscope optical head such as to maintain the image provided by the microscope always properly centered relative to the operating site.

These objects are attained by a device for automatically positioning and centering the optical head of a microscope for surgical use, the optical head being connected to a drive unit, characterised in that the device analyzes the image framed by the microscope objective by means of an automatic system for analyzing the image light distribution, then processes it until a reference point of the light distribution is identified, then on the basis of information regarding the position of the reference point of the light distribution it controls the drive unit of the microscope optical head.

During the operation the surgeon has available means (for example a fiber optic endoscopic probe) for illuminating, or concentrating a light beam onto, the zone in which he or one is operating. The result is that, very roughly, the site of the operation corresponds to the most illuminated zone. On the basis of this assumption the device of the present invention seeks, within the image framed by the microscope objective, the zone or point of highest light intensity, and makes that zone or point correspond to the site of the operation. Alternatively, in a preferred embodiment of the present invention, the device of the present invention calculates the position in horizontal and vertical coordinates of the luminous barycenter of the image as the parameter for locating the operating site with respect to a Cartesian reference system rigid with the microscope optical head.

The surgical microscope to which the device of the present invention can be connected must be provided with at least one image divider, so that the same image which the surgeon has before his or her eyes can be fed to an automatic image analysis system.

The automatic image analysis system can, for example, be a videocamera connected to an electronic image processing circuit or a photosensitive matrix connected to a microprocessor. The videocamera can be either in black and white, providing a standard black/white CCIR signal, or in color.

A microprocessor for processing the acquired images can be connected to the image analysis system as heretofore described. This connection can be either direct, without intermediate accessories, or an image memory device can be interposed, from which the microprocessor withdraws the image for analysis subsequent to the time at which the image was acquired and memorized.

In this case a system memory, a system bus with switching devices and an image acquisition card are connected to the videocamera, that card sampling the video signal and memorizing it in a memory bank in the form of an image matrix.

The processed signal from the videocamera, possibly reproduced on a television monitor for explanation and teaching purposes, is then analyzed in parallel by the electronic processing circuit.

BRIEF DESCRIPTION OF THE DRAWING

To better understand the operation of the centering device of the present invention, reference should be made to the accompanying drawing in which.

The sole FIGURE.

DETAILED DESCRIPTION

Figure 1:
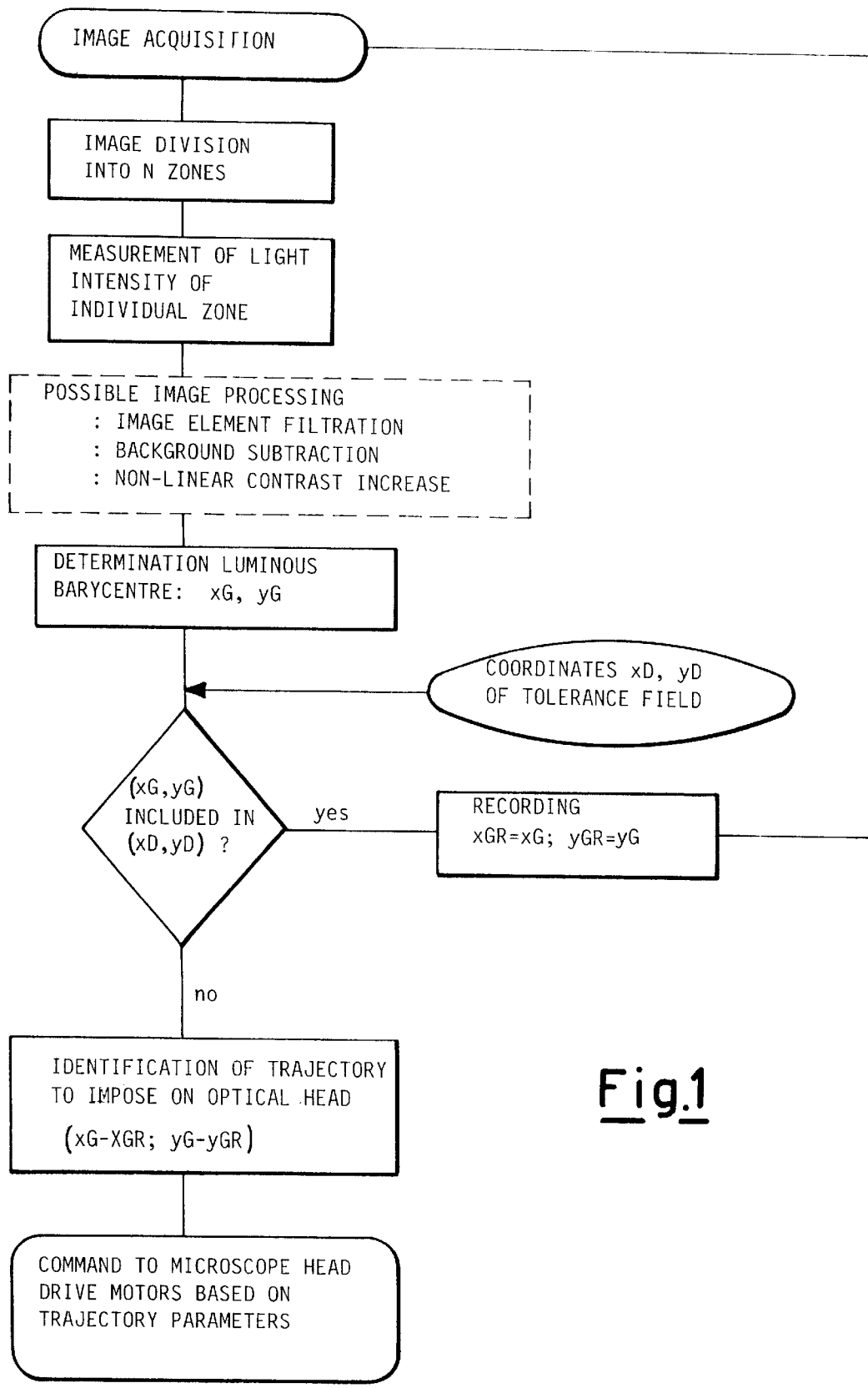
FIG. 1, shows the flow diagram of the actions performed by the device of the present invention.

The microprocessor forming part of the device analyzes the image produced by the videocamera and divides that image into N zones or frames. For each of these N zones or frames the microprocessor measures the light level and memorizes it. Hence, with each zone there is associated a value corresponding to the light intensity level of the zone.

After possible additional operations involving light level adjustment, light filtration, possible contrast increase, and subtracting the mean light level of the N zones, the microprocessor is able to calculate the position of the image "luminous barycenter" relative to the system of cartesian axes associated with the microscope optical head. The "luminous barycenter" means the barycenter calculated by assigning to each discrete zone a weight equal to its light level.

The greater the number of zones into which the video or digitalized image, is divided the greater the accuracy in identifying the position of said barycenter.

In an alternative form of the present invention, the electronic circuit seeks the brightest point of the image as the center of the brightest zone of the image, and defines this as the reference point of the image light distribution.

An advantage of the method is that no particular detail of the image has to be recognized and localized in terms of form, scale factor, orientation or chromatic composition, but only a reference point for the luminosity of the scene. This means that the calculation procedures are enormously simplified and accelerated, so as to take place in real time. In this manner, the tracking efficiency is largely independent of the effective magnification used, the background brightness, any chromatic dominance, etc. An additional possibility of seeking and precisely identifying the surgical site is to place on it a distinctive sign, for example an arrow, a geometrical shape, a cross, etc. of color or brightness which is considerably different from the surrounding operational environment, of any material suitable for the purpose. The microprocessor provided with the device of the invention must then be designed to recognize at least one shape and/or one color and possibly a light distribution orientation within the image.

This can be achieved, for example, by identifying the contours of an entirely connected zone of sufficiently uniform brightness and/or color, possibly gradually defining those contours ever more precisely, using conventional recognition algorithms. Upon completing this procedure, the resultant connected shape is compared with the previously memorized shape to be found. If there is sufficient similarity between the two shapes, the microprocessor completes the procedure for identifying the distinctive sign, otherwise, the microprecessor repeats the procedure until identification is achieved.

In this manner, the microprocessor is able to associate the exact position of the site to be framed with the recognition of a particular geometrical shape or its possible spatial orientation.

In preferred embodiments of the present invention, the image light distribution is analyzed within a specific spectral band, using wavelength-selective optical filters.

In a much preferred embodiment, that specific spectral band is located within the visible region of optical radiation, that spectral band having any desired width, so as to include only one color or several colors. In preferred embodiments alternative to this latter alternative, that spectral band is located either in the infrared region or in the ultraviolet region of optical radiation.

At this point, after the indicated procedures, the microprocessor has calculated the coordinates xG and yG within the cartesian reference system rigid with the optical head of the surgical microscope, and having its origin at the geometrical center of the visual field of the image light distribution reference point, whether this be the luminous barycenter or the brightest point. The microprocessor now checks whether that reference point lies within or outside a predetermined tolerance zone. The tolerance zone is represented, for example by coordinates ±|xd| and ±|yD|, or by a single coordinate pD in polar coordinates, determined previously. If it is found that the reference point falls within the tolerance zone, this means that the image is sufficiently centered and there is no need to feed any signal to the optical head drive unit. If, instead, the reference point does not fall within the tolerance zone, the device has to generate a signal which is then fed to optical head drive unit, which signal must be able to move the microscope optical head until the luminous barycenter of the image again falls within the tolerance zone.

To achieve this, the fastest way is to evaluate the extent and direction (the movement vector) of the movement undergone by the reference point from its previous position (the coordinates of the already estimated reference point being automatically memorized each time the image analysis and processing procedure is repeated).

When the movement vector has been evaluated, the command given to the drive unit is such as to copy the movement vector, i.e. such as to transmit to the microscope optical head a movement coherent with the movement vector (same direction, same modulus and same sense). In this manner, the image is rapidly and effectively recentered on the operating site.

Alternatively, in a second preferred embodiment of the device of the present invention, the movement vector can be evaluated in a slightly different manner, by taking it as the vector joining the center of the tolerance zone (defined by the two coordinates xDC=0; yDC=0) and the last calculated reference point.

Again in this case, the command given to the drive unit is such as to copy the movement vector.

The optical head drive unit is composed of electric motors connected to suitable reduction gears. The electric motors receive their commands from the microprocessor. If the microprocessor is not provided, the image processing circuit can be suitably modified so that it transmits commands to the electric motors to correctly reposition the optical head.

At this point the described image acquisition and processing procedure can be repeated.

The precision and accuracy of the device of the present invention in always returning the microscope optical head to a position such as to ensure image centering on the operation site is also a function of the calculation speed. For equal microprocessor processing capacity and speed, the calculation speed is an inverse function of the number of zones into which the image has been divided. For reasons of symmetry it is advisable for the number of zones to be a perfect square (64, 81, 100 etc.). As the number of zones increases the processsing time increases. However, with a large number of zones the resolution and the calculation time can be easily reduced by grouping the zones, into groups of 4 or 9 or another number, using software.

In a preferred embodiment of the invention, the sampling of the image and of the position of the barycenter is done at television frame frequency (50 Hz in Europe), whereas the head traversing times is given by the speed of the motors, which are usually fairly slow.

This means that the slow stage of the process of image recentering on the operating site is controlled neither by the image acquisition and processing procedure nor by the motor speed or the speed of the chosen optical head drive system.

In an alternative embodiment to the aforedescribed, the automatic system for analyzing the image light distribution comprises a photosensitive element arranged to generate signals proportional to the extent of off-centering of the image light distribution from the center of the photosensitive element, the off-centering being suitably measured along two mutually perpendicular directions.

Depending on the particular case, the photosensitive element can consist of a position-sensitive semiconductor photodiode, an optoelectronic sensor of quadrant or otherwise segmented type, or an optoelectronic image dissector tube.

To make the identification of the reference point in the form of the brightest point or the luminous barycenter of the image simpler and more reliable, it can be advantageous to provide means for increasing the diffusivity and/or reflectivity to optical radiation of all or part of the image. For example, the means can consist of diffusive or reflecting marker elements positioned within the image framed by the microscope objective.

In a preferred embodiment of the present invention, the means for increasing the diffusivity and/or reflectivity to optical radiation of all or part of the image. consist of the actual surgical instruments and devices used for the operation, suitably treated to be of greater brightness.

In this description, reference has so far been made only to the use of the surgical microscope controlled by the device of the present invention for ophthalmic surgery, and in particular vitreo-retinal surgery.

It should, however, be noted that the device of the present invention can be of help in any surgical operation with the aforedescribed problems and requirements. Neurosurgery and reconstructive plastic surgery can be mentioned as examples.

The device of the present invention can also be applied in an industrial field where microscopic investigations are required with the aid of endoscopic illumination, for example in electronics, and in the preparation of components such as thick film and thin film printed circuits.

What is claimed is:

1. A device for automatically positioning and centering an optical head of a medical microscope having an objective arranged for framing a movable image, comprising:

a drive unit arranged for laterally moving said objective so as to vary framing of the movable image; and an automatic image analysis system including a microprocessor arranged for identifying the position of a single reference point, said automatic image analysis system arranged for analyzing for light distribution of the movable image framed by said objective, for processing said light distribution to obtain the single reference point of light distribution, and for controlling said drive unit as a function of said reference point for achieving and maintaining a centered relationship of said reference point relative to said optical head.

2. The device of claim 1, wherein:

said automatic image analysis system includes a video camera operatively connected to an electronic image-processing circuit for providing a video signal from said video camera thereto.

3. The device of claim 2, wherein:

said automatic image analysis system further includes, operatively connected switch said video camera, a microprocessor, a system memory, a system bus, switching devices, and an image acquisition card arranged for sampling said video signal and to obtain a sample, and for storing said sample in said memory as an image matrix.

4. The device of claim 2, wherein:

said drive unit includes a plurality of electric motors operatively connected by reduction gearing to said optical head and arranged for receiving commands from said electronic circuit.

5. The device of claim 1, wherein:

said automatic image analysis system includes a photosensitive matrix operatively connected to a microprocessor.

6. The device of claim 5, wherein:

said microprocessor is arranged to identify the position of said single reference point of light distribution by recognizing at least one of a specific shape and an orientation of localized difference in light distribution within said image.

7. The device of claim 1, wherein said image has a luminous baricenter, and:

said automatic image analysis system is arranged to obtain as said single reference point, said luminous baricenter of said image.

8. The device of claim 7, wherein:

said automatic image analysis system includes a microprocessor arranged for identifying the position of said single reference point, by dividing the image into a given number of zones, measuring light level in each of said zones, and for calculating said luminous barycenter by assigning to each said zone a weight which depends on the respective light level in each zone.

9. The device of claim 8, wherein:

said microprocessor of said automatic image analysis system is arranged for subtracting from said light levels in each of said zones as measured, the mean light level of all of said zones before performing and calculating.

10. The device of claim 1, wherein said image has a brightest point, and:

said automatic image analysis system is arranged to obtain as said single reference point said brightest point of said image.

11. The device of claim 10, wherein:

said automatic image analysis system includes a microprocessor arranged for identifying the position of said single reference point, by dividing the image into a given number of zones, measuring light level in each of said zones, and for calculating said brightest point by assigning to each said zone a weight which depends on the respective light level in each zone.

12. The device of claim 1, wherein:

said automatic image analysis system includes a microprocessor arranged for identifying the position of said single reference point, by dividing the image into a given number of zones, measuring light level in each of said zones, and for calculating one of a luminous baricenter and a brightest point of said image by assigning to each said zone a weight which depends on the respective light level in each zone; and said zones are arranged in a square array having an equal number of zones per side.

13. The device of claim 1, wherein:

said automatic image analysis system is arranged for analyzing for light distribution the image formed by said objective, within a specific spatial band, by imposing wavelength-sensitive optical filtration on said image.

14. The device of claim 1, wherein:

said automatic image analysis system is arranged for analyzing light distribution the image formed by said objective, within the visible region of optical radiation, by imposing wavelength-sensitive optical filtration on said image.

15. The device of claim 1, wherein:

said automatic image analysis system is arranged for analyzing light distribution the image formed by said objective, within the visible infrared region of optical radiation, by imposing wavelength-sensitive optical filtration on said image.

16. The device of claim 1, wherein:

said automatic image analysis system is arranged for analyzing light distribution the image formed by said objective, within the visible ultraviolet region of optical radiation, by imposing wavelength-sensitive optical filtration on said image.

17. The device of claim 1, wherein:

said automatic image analysis system includes a microprocessor arranged for identifying the position of said single reference point, by dividing the image into a given number of zones, measuring light level in each of said zones, and for calculating one of a luminous baricenter and a bright point of said image by assigning to each said zone a weight which depends on the respective light level in each zone;

said automatic image analysis system being arranged to provide said controlling by being arranged to perform a check to determine whether said single reference point of light distribution lies within a predetermined tolerance zone, and, if not, for calculating a movement vector and operating said drive unit for causing said optical head to move along said movement vector so as to cause said single reference point of light distribution to lie within said predetermined zone.

18. The device of claim 17, wherein:

said automatic image analysis system is arranged to calculate said movement vector by making successive determinations of location of said single reference point of light distribution.

19. The device of claim 17, wherein said tolerance zone has a center, and:

said automatic image analysis system is arranged to calculate as said movement vector a vector joining said center of said tolerance zone and the location of said single reference point of light distribution.

20. The device of claim 1, wherein:

said automatic image analysis system is arranged to acquire information as to the light distribution of the image formed by said objective by including a photosensitive element having a center and arranged to generate signals proportional to the extend of off-centering of said light distribution along two mutually perpendicular axes, from said center of said photosensitive element.

21. The device of claim 20, wherein:

said photosensitive element is a position-sensitive semiconductor diode.

22. The device of claim 20, wherein:

said photosensitive element is one of a quadrant optoelectronic sensor and a segmented optoelectronic sensor.

23. The device of claim 20, wherein:

said photosensitive element is an optoelectronic image dissector tube.

24. The device of claim 20, wherein:

said drive unit includes a plurality of electric motors operatively connected by reduction gearing to said optical head and arranged for receiving commands from said microprocessor.

25. The device of claim 1, further comprising:

means applicable to the image for increasing at least one of diffusivity and/or reflectivity of the image to optical radiation.

26. The device of claim 25, wherein:

said means applicable to the image comprise at least one diffusive or reflective marker arranged to be positioned within the image framed by said objective.

27. The device of claim 25, wherein:

said means applicable to the image comprise a surgical instrument.

28. The device of claim 27, wherein:

said instrument is an instrument configured for use in performing opthalmic surgery.

29. The device of claim 27, wherein:

said instrument is an instrument configures for use performing vitreo-retinal surgery.

30. The device of claim 27, wherein:

said instrument is an instrument configured for use in performing neurosurgery.

31. The device of claim 27, wherein:

said instrument is an instrument configured for use in plastic surgery.

* * * * *